United States Patent [19]

Yamamoto et al.

[11] 4,193,932

[45] Mar. 18, 1980

[54] PROCESS FOR PREPARING ORGANIC ISOCYANATES

[75] Inventors: Ryuichi Yamamoto, Enmeiji; Kousuke Yamamoto, Toritsuka; Teruyuki Nagata, Kamishirakawa; Kenji Obata, Toritsuka, all of Japan

[73] Assignee: Mitsui Toatsu Chemicals Inc., Tokyo, Japan

[21] Appl. No.: 955,266

[22] Filed: Oct. 27, 1978

[30] Foreign Application Priority Data

Nov. 11, 1977 [JP] Japan ................................ 52-134692

[51] Int. Cl.$^2$ ........................................... C07C 118/02
[52] U.S. Cl. ........................ 260/453 PH; 260/453 SP; 260/939
[58] Field of Search ..................... 260/453 PH, 453 SP

[56] References Cited

U.S. PATENT DOCUMENTS

| 2,620,349 | 12/1952 | Slocombe | 260/453 SP |
| 3,219,678 | 11/1965 | Kober et al. | 260/453 SP |
| 3,234,253 | 2/1966 | Cooper | 260/453 PH |
| 3,549,504 | 12/1970 | Adica et al. | 260/453 SP |
| 3,857,871 | 12/1974 | Hatfield, Jr. et al. | 260/453 SP |

Primary Examiner—Dolph H. Torrence

[57] ABSTRACT

An improved process for preparing organic isocyanates is disclosed. An organic amine is reacted with phosgene to yield a reaction product, through which hydrogen chloride gas is passed in the presence of an inert organic solvent whereby the gas included in the reaction product is removed and the acid substances and hydrolyzable chlorine-containing substances included therein are minimized.

15 Claims, No Drawings

PROCESS FOR PREPARING ORGANIC ISOCYANATES

BACKGROUND OF THE INVENTION

This invention relates to an improvement in the preparation of an organic isocyanate and, more particularly, to an improved process for preparing an organic isocyanate by the reaction of an organic amine with phosgene wherein the acid substances and hydrolyzable chlorine-containing substances included in the reaction product are minimized.

Organic isocyanates, which are highly reactive compounds, are being widely used for the manufacture of polyurethane foams, elastomers, adhesives, paints, and the like.

While a number of processes for preparing organic isocyanates are known, one of the commonly used processes comprises reacting an appropriate amine with phosgene in the presence of an inert organic solvent to form an isocyanate, degassing the reaction mixture, recovering the solvent, and purifying the reaction product as required. The isocyanate thus obtained, especially a crude one, is contaminated with impurities including acid substances and hydrolyzable chlorine-containing substances. Since such impurities exercise a remarkably adverse effect on the reactivity of the isocyanate in the manufacture of polyurethanes, it is very important to remove or minimize them.

The aforesaid hydrolyzable chlorine-containing substances are considered to result chiefly from various side reactions taking place during the formation of the isocyanate or from the impurities included in the starting materials. For example, in the preparation of polymethylene polyphenyl polyisocyanate, the appropriate polyamine contains trace amounts of secondary amine. This secondary amine reacts with phosgene to form secondary carbamyl chloride.

In addition, various side reactions take place during the reaction of the polyamine with phosgene. For example, the amine reacts with the isocyanate to form polymers having urea(—NHCONH—) residue, which further react with phosgene to form allophanyl chlorides (secondary carbamyl chlorides).

These secondary carbamyl chlorides are relatively stable. That is to say, while the primary carbamyl chloride which is an intermediate in the course of the formation of an isocyanate from an organic amine and phosgene decomposes rather easily at elevated temperatures to give an isocyanate, the secondary carbamyl chlorides are very difficult to decompose.

In order to remove hydrolyzable chlorine-containing substances as described above, it is a common practice to pass nitrogen gas through the reaction product of an organic amine with phosgene at elevated temperatures and thereby drive away the unreacted phosgene, hydrogen chloride, and hydrolyzable chlorine-containing substances dissolved in the reaction product.

The content of such impurities will be substantially reduced if the reaction product treated as above is further distilled prior to practical use. In the case of high boiling isocyanates, however, the reaction product cannot be purified by distillation. Accordingly, it is highly desirable to remove the hydrolyzable chlorine-containing substances without resorting to distillation.

Moreover, in order that such hydrolyzable chlorine-containing substances may be removed as much as possible from the reaction product of an organic amine with phosgene, it is necessary to degas the reaction product at higher temperatures for a relatively long period of time. However, when exposed to high temperatures for a long period of time, isocyanates tend to polymerize and hence cause an undesirable increase in viscosity. Especially in the case of polymethylene polyphenyl polyisocyanate, remarkable changes in viscosity and molecular weight distribution of lower polymer may result.

In order to overcome the above-described difficulties, for example, Japanese Patent Publication No. 29841/'71 discloses a process which involves introducing an inert gas into the reaction product under pressure. Moreover, Japanese Patent Application Disclosure No. 23745/'73 and No. 76839/'73 propose a process which involves passing the reaction product through a packed tower in counterflow with an inert gas stream. However, these processes are undesirable from an economical viewpoint because of an unduly large consumption of inert gas and, moreover, are still incapable of eliminating the disadvantage that the isocyanate tends to polymerize. Thus, they are hardly considered to be practicable in industrial applications.

SUMMARY OF THE INVENTION

It is an object of this invention to provide an improved process for preparing organic isocyanates which process enables one to minimize the acid substances and hydrolyzable chlorine-containing substances included in the reaction product of an organic amine with phosgene.

It is another object of this invention to provide an improved process for preparing organic isocyanates which process enables one to minimize the acid substances and hydrolyzable chlorine-containing substances included in the reaction product by treating the reaction product for a long period of time without causing polymerization of the isocyanate.

It is still another object of this invention to provide an improved process for preparing organic isocyanates which process enables one to minimize the acid substances and hydrolyzable chlorine-containing substances included in the reaction product comprising an organic isocyanate that is incapable of being purified especially by distillation.

In accordance with this invention, there is provided an improved process for preparing organic isocyanates which comprises reacting an organic amine with phosgene to yield a reaction product containing the corresponding organic isocyanate and then subjecting the reaction product to purification. In the process of the invention, the improvement comprises passing hydrogen chloride gas through the reaction product in the presence of an inert organic solvent whereby the gas included in the reaction product is removed and the acid substances and hydrolyzable chlorine-containing substances also included therein are minimized.

DETAILED DESCRIPTION OF THE INVENTION

The treatment of the reaction product with hydrogen chloride gas is carried out in the presence of an inert organic solvent. The inert organic solvent used for this purpose may be any of the organic solvents that are commonly used in the preparation of organic isocyanates. Specific examples of suitable organic solvents are benzene, toluene, xylene, chlorotoluenes, chlorobenzene, and dichlorobenzenes, among which dichlorobenzenes are preferred. The concentration of the reaction product in the inert organic solvent is from 3 to 50% by weight and preferably from 10 to 30% by weight.

In order to pass hydrogen chloride gas through the reaction product of an organic amine with phosgene, any of the various methods well known in the art can be used. It is preferable, however, that the reaction product is introduced into a packed column where it is heated and brought into contact with hydrogen chloride gas being supplied in counterflow therewith. The hydrogen chloride gas may be used in combination with an inert gas such as nitrogen gas, though it is not necessary in ordinary cases. The time required for the treatment depends on the temperature at which the treatment is carried out. Preferably, the treatment is carried out at a temperature of from 140° to 230° C. for a period of from 0.5 to 5 hours. The total amount of hydrogen chloride gas which is used in the above treatment is preferably from 0.5 to 100 l per 1.0 Kg of the solution of the reaction product in the inert organic solvent. At temperatures higher than the boiling point of the inert organic solvent used or the isocyanate formed, the treatment is carried out under pressure.

In a plant for the manufacture of organic isocyanates, hydrogen chloride gas is generated in large quantities (because hydrogen chloride is formed in an amount of 2 moles per equivalent of amine groups). This hydrogen chloride gas contains unreacted phosgene, which can be recovered by absorbing it in a solvent. The hydrogen chloride gas thus freed of unreacted phosgene, which still contains trace amounts of phosgene and solvent, may be directly used in the process of the invention. The use of such hydrogen chloride gas permits the phosgene dissolved in the reaction product to be driven away, resulting in a higher recovery of phosgene and a higher degree of utilization of hydrogen chloride gas. This makes the process of the invention very suitable for industrial purposes.

The organic isocyanates which can be prepared by the process of the invention include, for example, tolylene diisocyanates (such as 2,4- and 2,6-isomers and mixtures thereof), diphenylmethane diisocyanates (such as 4,4'-, 2,4'- and 2,2'-isomers and mixtures thereof), triphenylmethane triisocyanate, polymethylene polyphenyl polyisocyanate, naphthylene diisocyanate, 3,3'-dimethylbiphenyl-4,4'-diisocyanate, xylidine diisocyanate, tris (4-isocyanatophenyl) thiophosphate, hexamethylene diisocyanate, tetramethylene diisocyanate, cyclohexylene diisocyanate, methylene bis (cyclohexyl isocyanate), and the like. However, the organic isocyanates which are preferably prepared by the process of the invention are aromatic isocyanates, especially having a boiling point above 140° C. Among others, the process of the invention is more preferably applied to the preparation of polymethylene polyphenyl polyisocyanate, triphenylmethane triisocyanate, and tris(4-isocyanatophenyl) thiophosphate, and most preferably to the preparation of polymethylene polyphenyl polyisocyanate.

In contrast to the conventional processes in which the reaction product is treated with an inert gas, the process of the invention enables one to economically and easily minimize the acid substances and hydrolyzable chlorine-containing substances without causing polymerization of the isocyanate. Especially in the case of polymethylene polyphenyl polyisocyanate which is used without being purified by distillation, the presence of isocyanate polymers will exert a delicate influence on the manufacture of polyurethane foams and the properties thereof. Since the formation of such polymers is suppressed in the polymethylene polyphenyl polyisocyanate prepared by the process of the invention, the resulting polyurethane foams can naturally be expected to have improved physical properties. It was suprising, however, that such polyurethane foams have proved to be markedly improved in adhesion properties, dimentional stability, and color. For example, the polyurethane foams used for the manufacture of sandwich panels are required to have particularly good adhesion properties. In making sandwich panels, the polymethylene polyphenyl polyisocyanate prepared by the process of the invention has been found to provide more excellent adhesion properties than that prepared by any conventional process. Moreover, the rigid polyurethane foams for heat insulating material of electric refrigerators require good dimentional stability to low temperatures. The polymethylene polyphenyl polyisocyanate prepared by the process of the invention has been found to provide polyurethane foams having improved dimensional stability at low temperatures. Furthermore, certain applications require polyurethane foams having the least possible degree of coloration, but the formation of isocyanate polymers will undesirably cause the resulting polyurethane foams to become colored to an undue extent. Since the formation of such polymers is suppressed, the polymethylene polyphenyl polyisocyanate prepared by the process of the invention has been found to show only a slight increase in viscosity and provide polyurethane foams having a lighter shade of color. It has been utterly impossible to foresee these remarkable effects of the invention on the basis of the prior art. Thus, it is an outstanding feature of the invention that the polymethylene polyphenyl polyisocyanate prepared by the process of the invention can be applied to a wide range of uses.

The invention will be more clearly understood by reference to the following examples. They are intended to illustrate the practice of the invention and are not to be construed to limit the scope of the invention. In these examples, the content of hydrolyzable chlorine-containing substances was determined according to the method of ASTM D1638-59T.

EXAMPLE 1

A condensation product of aniline, formaldehyde, and hydrogen chloride (in the molar ratio of 1.80:1.0:1.3), which comprised 55% by weight of diaminodiphenylmethane and 45% by weight of polymethylene polyphenyl polyamines, was diluted with o-dichlorobenzene to a concentration of 7% by weight, reacted with an excess of phosgene at temperatures below 20° C., heated to a temperature of 150° C., and again reacted with an excess of phosgene.

Then, 500 g of the reaction mixture was degassed at a temperature of 170° C. and atmospheric pressure by passing hydrogen chloride gas therethrough at a rate of 300 ml/min. for a period of 2 hours. The hydrogen chloride gas was a by-product generated by the above-mentioned reaction of the organic amine with phosgene. The degassed reaction mixture was a pale yellow and clear liquid which was more lightly colored than and evidently different in shade from that of the succeeding Control 1.

Thereafter, the degassed reaction mixture was distilled at reduced pressure to remove the solvent. The crude polymethylene polyphenyl polyisocyanate thus obtained had a viscosity of 56 centipoises (at 25° C.) and contained 31.0% of isocyanate (NCO) groups, 0.112% of acid substances, and 0.161% of hydrolyzable chlorine-containing substances.

Control 1

For purposes of comparison, the procedure of Example 1 was repeated except that the hydrogen chloride gas was replaced by nitrogen gas. The degassed reaction mixture, which was considerably colored in brown, was distilled at reduced pressure to remove the solvent. The crude polymethylene polyphenyl polyisocyanate thus obtained had a viscosity of 87 centipoises (at 25° C.) and contained 30.8% of isocyanate (NCO) groups, 0.127% of acid substances, and 0.180% of hydrolyzable chlorine-containing substances.

The crude polymethylene polyphenyl polyisocyanates prepared in Example 1 and Control 1 were compared in color. Specifically, a 1% solution of each sample in anhydrous toluene was placed in a cell having an optical path length of 10 mm and its absorbance was measured at a wavelength of 430 m$\mu$ by means of a spectrophotometer. The results were 0.130 for the crude polymethylene polyphenyl polyisocyanate of Example 1 and 0.235 for that of Control 1, which clearly indicates that the product of Example 1 was colored to a lesser extent.

Then, these polymethylene polyphenyl polyisocyanates were used to make polyurethane according to the following three formulations.

| Formulation A | |
| --- | --- |
| Ingredient | Parts by Weight |
| PPG-TR-500 (polyether polyol having an OH value of 490; manufactured by Mitsui-Nisso Urethane Co.) | 70 |
| PPG-AE-300 (polyether polyol having an OH value of 755; manufactured by Mitsui-Nisso Urethane Co.) | 30 |
| Trichloromonofluoromethane (blowing agent) | 47 |
| Water | 1.5 |
| Silicone SH-193 (manufactured by Toray Silicone Co.) | 1.0 |
| Triethylenediamine (33% solution in dipropylene glycol) | 4.0 |
| Trichloroethyl phosphate (flame retarder) | 20 |
| Polymethylene polyphenyl polyisocyanate (sample) | 170 |

This formulation had an NCO index (molar ratio of NCO to OH groups) of 1.05. A piece of liner paper was provided for use as facing material and an aluminum mold (300 mm × 300 mm × 50 mm) was placed thereon. The above ingredients were mixed, poured into the mold, and allowed to foam. The resulting polyurethane foam was then tested for peel strength by means of a push-pull scale.

Table 1

| Test Results of Formulation A | | |
| --- | --- | --- |
| | Crude Polymethylene Polyphenyl Polyisocyanate | |
| | Example 1 | Control 1 |
| Foaming Time | | |
| Initiation Time (sec.) | 7 | 9 |
| Tack-free Time (sec.) | 44 | 48 |
| Peel Strength (Kg.) | | |
| After 6 min. | 1.15 | 0.65 |
| After 1 hr. | 1.15 | 0.70 |

Table 1-continued

| Test Results of Formulation A | | |
| --- | --- | --- |
| | Crude Polymethylene Polyphenyl Polyisocyanate | |
| | Example 1 | Control 1 |
| After 20 hr. | 1.15 | 0.70 |

As is evident from Table 1, the polyurethane foam resulting from the crude polymethylene polyphenyl polyisocyanate prepared by the process of the invention was improved in adhesion properties.

| Formulation B | |
| --- | --- |
| Ingredient | Parts by Weight |
| PPG-SU450LA (polyether polyol having an OH value of 450; manufactured by Mitsui-Nisso Urethane Co.) | 100 |
| Trichloromonofluoromethane (blowing agent) | 41 |
| Silicone L-5350 (foam stabilizer; manufactured by Nippon-Unica Co.) | 1.5 |
| Tetramethylhexamethylenediamine | 25 |
| Dimethylethanolamine (catalyst) | 1.5 |
| Polymethylene polyphenyl polyisocyanate (sample) | 115.0 |

This formulation had an NCO index of 1.05. The above ingredients were mixed and allowed to foam. The resulting polyurethane foam was tested for physical properties.

Table 2

| Test Results of Formulation B | | |
| --- | --- | --- |
| | Crude Polymethylene Polyphenyl Polyisocyanate | |
| | Example 1 | Control 1 |
| Initiation Time (sec.) | 31 | 33 |
| Tack-free Time (sec.) | 48 | 54 |
| Density (g/cm$^3$) | 0.0285 | 0.0286 |
| Compression Strength (kg/cm$^2$) | | |
| Longitudinal | 2.21 | 2.23 |
| Transverse | 1.22 | 0.90 |
| Dimentional Stability (%) | | |
| Wet Heat Condition (70° C., 100%, 72 hr.) | | |
| Longitudinal | −0.2 | −1.4 |
| Transverse | 2.9 | 8.4 |
| Dry Heat Condition (110° C., 74 hr.) | | |
| Longitudinal | −0.6 | −1.20 |
| Transverse | 2.0 | 9.4 |
| Low Temperature Condition (−20° C., 72 hr.) | | |
| Longitudinal | 0 | −0.4 |
| Transverse | −0.2 | −3.5 |
| Color of Foam | Pale Yellow | Brown |

As is evident from Table 2, the polyurethane foam resulting from the polymethylene polyphenyl polyisocyanate prepared by the process of the invention was improved in dimensional stability under wet heat, dry heat, and low temperature conditions as well as in compression strength and color.

| Formulation C | |
| --- | --- |
| Ingredient | Parts by Weight |
| PPG-EP240 (polyether polyol having an OH value of 25; manufactured by Mitsui-Nisso Urethan Co.) | 150 |
| Triethylenediamine (33% solution in dipropylene glycol) | 0.1 |

| -continued | |
|---|---|
| Formulation C | |
| Ingredient | Parts by Weight |
| Polymethylene Polyphenyl Polyisocyanate (sample) | 8.8 |

This formulation had an NCO index of 1.0. The above ingredients were mixed and the rate of gelation of the mixture was measured by means of a Brookfield type viscometer. The results are expressed as viscosities in centipoises.

Table 3

| Rate of Gelation of Formulation C | | |
|---|---|---|
| Sample | Crude Polymethylene Polyphenyl Polyisocyanate | |
| Time (min.) | Example 1 | Control 1 |
| 2 | 1.620 | 1.540 |
| 4 | 2.000 | 1.820 |
| 6 | 2.600 | 2.400 |
| 8 | 3.400 | 3.040 |
| 10 | 4.600 | 4.020 |
| 12 | 6.000 | 5.400 |
| 14 | 8.000 | 7.080 |
| 16 | 10.800 | 9.400 |

As is evident from Table 3, the polymethylene polyphenyl polyisocyanate prepared by the process of the invention was improved in reactivity.

EXAMPLE 2

Tolylenediamine, which comprised 80% by weight of 2,4-isomer and 20% by weight of 2,6-isomer, was diluted with o-dichlorobenzene to a concentration of 7% by weight and reacted with phosgene in the same manner as described in Example 1.

Then, 500 g of the reaction mixture was degassed at a temperature of 170° C. and atmospheric pressure by passing hydrogen chloride gas therethrough at a rate of 100 ml/min. for a period of 2 hours. The hydrogen chloride gas was a by-product generated by the reaction of tolylene diamine with phosgene.

Thereafter, the degassed reaction mixture was distilled at reduced pressure to remove the solvent. The crude tolylene diisocyanate thus obtained was spectrophotometrically evaluated in the same manner as described in Example 1. As a result, this tolylene diisocyanate was found to have an absorbance of 0.22, which clearly indicates that the product of Example 2 was improved in color as compared with the product of the succeeding Control 2 having an absorbance of 0.38.

This crude tolylene diisocyanate was used to make a polyurethane foam according to the following formulation.

| Ingredient | Parts by Weight |
|---|---|
| PPG-SV-450M (polyether polyol having an OH value of 450; manufactured by Mitsui-Nisso Urethane Co.) | 100 |
| Trichloromonofluoromethane (blowing agent) | 37.2 |
| Silicone SH-193 (manufactured by Toray Silicone Co.) | 1.5 |
| Triethylenediamine (33% solution in dipropylene glycol) | 2.0 |
| Diethylethanolamine (catalyst) | 1.5 |
| Crude Tolylene Diisocyanate | 95.5 |

The resulting polyurethane foam appeared pale brownish yellow and proved to be more lightly colored than the polyurethane foam (light brown) resulting from the crude tolylene diisocyanate of the succeeding Control 2.

The remaining portion of the crude tolylene diisocyanate was further distilled at reduced pressure to yield a colorless and clear product. The resulting pure tolylene diisocyanate had a purity of 99.5% and contained 0.015% of hydrolyzable chlorine-containing substances and 0.004% of acid substances.

Control 2

For purposes of Comparison, the procedure of Example 2 was repeated except that the hydrogen chloride gas was replaced by nitrogen gas. The resulting pure tolylene diisocyanate had a purity of 99.5% and contained 0.013% of hydrolyzable chlorine-containing substances and 0.004% of acid substances.

I claim:

1. In a process for preparing an organic isocyanate including reacting an organic amine with phosgene to yield a reaction product containing the corresponding organic isocyanate and subjecting said reaction product to purification, the improvement which comprises passing hydrogen chloride gas through said reaction product in the presence of an inert organic solvent whereby the gas included in said reaction product is removed and the acid substances and hydrolyzable chlorine-containing substances included therein are minimized.

2. A process as claimed in claim 1 wherein the concentration of said reaction product in said inert organic solvent is from 3 to 50% by weight.

3. A process as claimed in claim 2 wherein the concentration of said reaction product in said inert organic solvent is from 10 to 30% by weight.

4. A process as claimed in claim 1 wherein said inert organic solvent is selected from the group consisting of benzene, toluene, xylene, chlorotoluenes, chlorobenzene and dichlorobenzenes.

5. A process as claimed in claim 1 wherein said organic isocyanate is an aromatic isocyanate.

6. A process as claimed in claim 5 wherein said aromatic isocyanate has a boiling point of at least 140° C.

7. A process as claimed in claim 5 wherein said aromatic isocyanate is selected from the group consisting of tris(4-isocyanatophenyl)thiophosphate, triphenylmethane triisocyanate, and polymethylene polyphenyl polyisocyanate.

8. A process as claimed in claim 5 wherein said aromatic isocyanate is polymethylene polyphenyl polyisocyanate.

9. A process as claimed in claim 1 wherein said hydrogen chloride gas is passed through said reaction product at a temperature of from 140° to 230° C.

10. A process as claimed in claim 9 wherein said hydrogen chloride gas is passed through said reaction product for a period of from 0.5 to 5 hours.

11. A process as claimed in claim 9 wherein said hydrogen chloride gas is passed through said reaction product in an amount of from 0.5 to 100 l per 1.0 Kg of the solution of said reaction product in said inert organic solvent.

12. A process as claimed in claim 9 wherein said hydrogen chloride gas is introduced into a packed zone and brought into contact with the heated reaction product countercurrently.

13. A process as claimed in claim 1 wherein said hydrogen chloride gas comprises the hydrogen chloride by-product which has been generated by the reaction of said organic amine with said phosgene and then freed of unreacted phosgene.

14. In a process for preparing an aromatic isocyanate including reacting an aromatic amine with phosgene to form a reaction product containing the corresponding aromatic isocyanate and subjecting said reaction product to purification by contacting same with an inert gas to remove the gas contained in said reaction product and to lower the contents of the acid substances and hydrolyzable chlorine-containing substances contained in said reaction product, the improvement which comprises passing hydrogen chloride gas through said reaction product in the presence of an inert organic solvent at a temperature of from 140° C. to 230° C., whereby the gas included in said reaction product is removed and said acid substances and hydrolyzable chlorine-containing substances are minimized.

15. In a process for preparing an aromatic isocyanate selected from the group consisting of tris (4-isocyanato phenyl)thiophosphate, triphenylmethane triisocyanate, and polymethylene polyphenyl polyisocyanate, said process including reacting an aromatic amine with phosgene to form a reaction product containing said aromatic isocyanate and subjecting said reaction mixture to purification by contacting said reaction product with an inert gas to remove gas contained in said reaction product and to lower the contents of the acid substances and hydrolyzable chlorine-containing substances contained in said reaction product, the improvement which comprises passing hydrogen chloride gas through a solution containing 3 to 50% by weight of said reaction product, in an inert organic solvent, at a temperature of from 140° C. to 230° C., said hydrogen chloride gas being passed through said reaction product in an amount of from 0.5 to 100 liters per kilogram of said solution.

* * * * *